United States Patent [19]
Suzuki et al.

[11] Patent Number: 6,150,040
[45] Date of Patent: Nov. 21, 2000

[54] PURE STEAM-RELATED APPARATUS PROTECTED FROM FOULING AND METHOD OF MANUFACTURING THE SAME

[75] Inventors: Osamu Suzuki; Mikio Inoue; Toshio Sagara; Kenichi Osakabe; Masao Kawai, all of Yokohama, Japan

[73] Assignee: JGC Corporation, Tokyo, Japan

[21] Appl. No.: 09/078,497

[22] Filed: May 14, 1998

[30] Foreign Application Priority Data

May 15, 1997 [JP] Japan ........................ 9-125860
Mar. 16, 1998 [JP] Japan ....................... 10-065808

[51] Int. Cl.[7] ................... B32B 15/18; C23C 22/00
[52] U.S. Cl. .................. 428/667; 148/286; 148/287; 148/516; 148/519; 148/537; 201/18; 202/267.1; 203/86; 428/628; 428/629; 428/472.1; 428/472.22
[58] Field of Search .................. 428/628, 629, 428/667, 472.1, 472.2; 148/286, 287, 516, 519, 537; 201/18; 202/267.1; 203/86

[56] References Cited

U.S. PATENT DOCUMENTS

| | | | |
|---|---|---|---|
| 2,357,219 | 8/1944 | Mott | 428/472.1 |
| 2,442,223 | 5/1948 | Uhlig | 148/286 |
| 4,518,440 | 5/1985 | Phillips, Jr. | 428/472.1 |

*Primary Examiner*—Deborah Jones
*Assistant Examiner*—Robert R. Koehler
*Attorney, Agent, or Firm*—Kubovcik & Kubovcik

[57] ABSTRACT

A pure steam-related apparatus, which is one of apparatus in the group of pure steam generators generating pure steam from purified water, pipelines for pure steam and sterilizers using pure steam, is protected from discoloration, so-called "fouling", to red or black caused by contact with the pure steam. The apparatus is manufactured by using an austenitic stainless steel sheet as the material, by taking the blanks from the material which received no mechanical surface polishing, by deforming and welding, without electrolytic polishing customarily done, and by passivating the surface to contact pure water to increase Cr-content in the passivation film to such extent as 45 atomic % or higher, preferably 55 atomic % or higher. Better results will be obtained by ensuring Cr/Fe ratio in the passivation film at the level of 1.45 or higher, preferably, 1.70 or higher.

8 Claims, 4 Drawing Sheets

PURE STEAM-RELATED APPARATUS PROTECTED FROM FOULING AND METHOD OF MANUFACTURING THE SAME

BACKGROUND OF THE INVENTION

The present invention concerns improvements in apparatus which treats pure steam, or steam prepared by evaporation of purified water, and provides the apparatus in which phenomenon of discoloration, which is called "fouling", on the surface of the apparatus which may occur after use over a long period of time.

Needless to say, water system is an important part of various industries such as biotechnology and pharmaceuticals. For example, water for injection and purified water must observe regulations by pharmaceutical codes, and sterilization by high pressure steam is carried out using pure steam. Pure water and pure steam are used also in some fields other than the above mentioned industries, such as food industry, fermentation and brewing, and cosmetics.

Pure steam is generated by distilling purified water, which in turn is prepared by purification methods such as deionization, reverse osmosis and ultrafiltration, and the pure steam-related apparatus such as pure steam generators, pipelines for passing the pure steam, sterilizer using the pure steam and condenser for obtaining condensed pure water are made with stainless steel, particularly, austenitic stainless steel which is of good processability. The material called "sanitary stainless" is used for manufacturing the pure steam-related apparatus in the state that it has been surface polished so as to eliminate unevenness which may be strongpoints for microorganisms to propagate. Polishing is usually carried out by combination of belt polishing using a fine abrasive grain of #180 or finer and subsequent buff polishing so that highly smooth surface may be obtained.

Pure steam is so corrosive that those in this technology often observe formation of "rouge" which is, as the name indicates, red metal oxide on the surfaces of the sanitary stainless products which are in contact with pure steam. This is reasonable in view of the fact that purified water has, as is called "hungry water", aggressive nature to produce corrosion on the surface of the metal. Formation of rouge must be prevented because the rouge may go into condensed water to damage water quality or contaminate the objects to be sterilized.

To cope with formation of the rouge it has been proposed to use the sanitary stainless treated by, following to the above mentioned mechanical polishing, electropolishing, or, instead of, or together with the electropolishing, passivating the surface of the apparatus (J. Villafranca et al., Pharm, Engineer., 5(6), 28–30, 1985). However, even with the electropolishing and passivation, it is still difficult to prevent occurrence of the rouge. Further, it was observed that discoloration to black occurs on the surface of the sanitary stainless. The black discoloration tends to occur at the parts where pure water formed by condensation of pure steam exists. These phenomena of staining the surfaces of sanitary stainless steel parts are in all called "fouling".

There are various views on the relation between the methods of surface treatment of austenitic stainless steel and corrosion thereof. The above noted proposal to electrolytically polish the surface is based on the report that corrosion resistance of the steel to pure hot water and pure steam will be improved when electropolishing is added after buff polishing in comparison with buff polishing only (K. Nagai, PHARM TECH JAPAN 11(13), 25, 1995). On the other hand, another researcher reported that Cr-content at the surface, which is believed to be an index of corrosion resistance, is higher in the passivated surface than in the electrolytically polished surface (M. Seo et al., Trans. Jpn. Inst. Met., 21(12), 805, 1980). Further, according to another report, oxidation treatment in gas phase and acid treatment in addition to the electropolishing decreases dissolution of the stainless by hot water, acid or alkaline solution (T. Tasaki et al., Kuki Seijo, 31(4), 232, 1993). Anyway, however, there has been established no effective method to prevent fouling or discoloration to red or black of the sanitary stainless surface.

As the temporary countermeasure it has been recommended and practiced, particularly in the United States, to repeat passivation treatment periodically after installation and operation of the apparatus related to pure steam. In Japan, such a treatment has not been established and seldom practiced. If the passivation after installation of the apparatus is to be practiced, it is necessary to introduce solution for passivation by pumping from a storage tank to process lines of the apparatus, to keep the apparatus under contact with the solution for a necessary period of time and to rinse the apparatus with water. When necessary, pumped circulation or heating the passivation solution in a jacketed storage tank will be added to the above operation. Anyway, re-passivation is a laborious operation. The spent passivation solution must be treated before discarding, and such treatment will require considerable cost.

SUMMARY OF THE INVENTION

The object of this invention is to expedite the present status of the technology concerning pure steam-related apparatus and to provide an improved pure steam-related apparatus and a method for manufacturing it, in which fouling on the surfaces of the stainless steel parts in contact with pure steam is prevented or at least reduced, and thereby to realize better safety in various industries such as pharmaceuticals production, and to reduce the costs by lightening burden of maintenance of the apparatus.

The pure steam-related apparatus protected from fouling according to the present invention is one of the apparatus of the group of pure steam generators generating pure steam from purified water, pipe lines for pure steam and sterilizers using pure steam, and is characterized in that the material used is an austenitic stainless steel, that the parts to contact pure steam are prepared by taking the blanks from a material which received no mechanical surface polishing, deforming and welding, and that the surface to contact pure water is passivated so as to heighten Cr-content in the passivation film to such extent as 45 atomic % or higher.

The method of manufacturing the pure steam-related apparatus according to the present invention is a method of manufacturing one of the apparatus of the above mentioned group and comprises the steps of taking blanks for parts to contact pure steam from an austenitic stainless steel sheet which received no mechanical surface polishing, forming parts from the blanks by necessary deformation and welding, and passivating the surface to contact pure steam of the parts so as to increase Cr- content in the passivation film to 45% or higher.

The phrase "received no mechanical surface polishing" is to mean that the steps of producing the stainless steel sheet may be hot rolling only, or hot rolling and cold rolling, to which bright annealing may be added, and that any smoothing processing which gives mechanical stress on the surface, such as buff polishing and sand blast, is excluded.

DETAILED EXPLANATION OF THE PREFERRED EMBODIMENTS

The Cr-content in the passivation film is preferably 55 atomic % or higher. Also, it is preferable that atomic ratio of Cr/Fe in the passivation film is 1.45 or higher. More preferable Cr/Fe ratio is 1.70 or higher.

Suitable austenitic stainless steels which may be used as the material for the present apparatus are one selected from the group of SUS 304, 304L, 316, 316L, 316N, 316J1, 316J1L, 317 and 317L.

Passivation may be carried out using nitric acid of 5 wt. % or higher and hydrofluoric acid of 1 wt. % or higher. One or more of acids other than nitric acid such as sulfuric acid, hydrochloric acid, phosphoric acid and citric acid may be used.

With respect to the mechanism of fouling, particularly red discoloration or the rouge, it is speculated that, even after passivation the scratches formed during buff polishing remains insufficiently passivated, and therefore, the change of Fe—$Fe_2O_3$ occurs, or that some of alumina-rich particles used as abrasive grains remain on the polished surface and they act as points for pit formation. As to the black discoloration, because it is often observed at the meniscus of the stainless steel parts, the inventors speculate that metals at the surface dissolve out as the ions, and hydroxides resulting from the ions are adsorbed on the surface and transform into oxides at the high temperature, i.e., Fe—Fe$(OH)_2$—$Fe_3O_4$. Analysis of the discoloration components revealed that the red substance consists essentially of hematite ($Fe_2O_3$), and the black substance consists mainly of magnetite ($Fe_3O_4$) and small amounts of Al, Si and P.

Under the circumstances we became doubtful as to whether mechanical polishing which has been believed necessary and customarily practiced to obtain highly smooth surface of the sanitary stainless is truly effective, but rather, an underlying cause of the fouling. Also we predicted that the structure of the passivation film has great influence on both occurrence and prevention of the fouling, and carried out the experiments mentioned below. As the results, it has been ascertained that, as expected, in the cases where passivation is done without mechanical polishing the fouling is reduced to be zero or nearly zero, and that, in order to substantially prevent the fouling it is necessary to ensure Cr-content in the passivation film at a certain level or higher. The inventors further discovered that it is preferable to maintain the atomic ratio of Cr/Fe in the passivation film at a certain level or higher.

EXAMPLES

Figure 1:
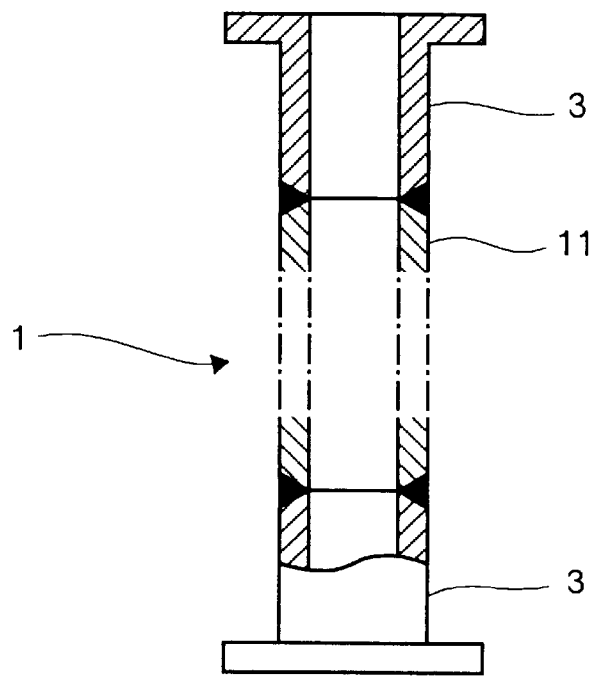
FIG. 1 illustrates, with partly sectional view, structure of a sample stainless steel straight tube manufactured in the example of the present invention.
Figure 2:
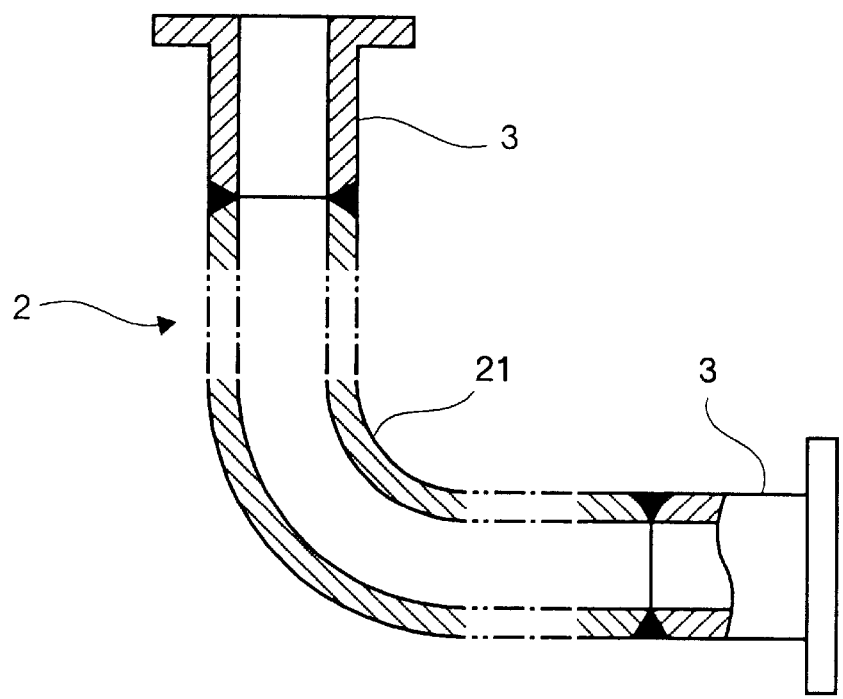
FIG. 2 illustrates, also with partly sectional view, structure of a sample stainless steel elbow manufactured in the example of the present invention.

Using a cold rolled austenitic stainless steel sheet as the material, "1.5S" straight tubes (1) as shown in FIG. 1 and "1.5" elbows (2) as shown in FIG. 2 were manufactured. The straight tubes are for observing the fouling caused by pure steam or in vapor phase, and the elbows are for observing the fouling caused by condensate of pure steam or in liquid phase. The body (11) of the straight tube and the body (21) of the elbow were prepared by rolling or rolling and bending followed by welding and bead-cutting. The ferrules (3) were prepared with the same material as the bodies and attached to the bodies by welding. The straight tubes are 200 mm long, inclusive of the ferrules, and one side of the elbows, 150 mm long. Thickness of both the samples is 1.2 mm and the inner diameter is 35.7 mm.

The samples were then subjected to various surface treatments as shown in Table 1. Material of the samples numbered 4 and 15 is SUS 304, and the material of the rest of the samples is SUS 316L. The ferrule was polished in the process of manufacturing by buff polishing (with #400 abrasive grit) and subsequent electropolishing. Conditions for the surface treatment are as follows:

Passivation A:
  soaking in an acid solution containing $HNO_3$ 10%+HF 3% at 50–60° C. for 30 seconds, followed by rinsing with water;

Passivation C:
  soaking in an acid mixture containing HCl 10%+$HNO_3$ 5%+$H_2SO_4$ 2.5%+aniline 0.2% at 85° C. for 30 seconds, followed by rinsing with water, and
  soaking in an acid solution containing $HNO_3$ 10%+HF 5% at room temperature for 60 seconds, followed by rinsing with water;

Passivation D:
  soaking in an acid mixture containing HCl 10%+$HNO_3$ 5%+$H_2SO_4$ 2.5%+aniline 0.2% at 85° C. for 30 seconds, followed by rinsing with water, and
  soaking in an acid solution containing $HNO_3$ 30%+HF 5% at room temperature for 60 seconds, followed by rinsing with water;

Passivation E:
  soaking in an acid mixture containing HCl 10%+$HNO_3$ 5%+$H_2SO_4$ 2.5%+aniline 0.2% at 85° C. for 30 seconds, followed by rinsing with water, and
  soaking in an acid solution containing $HNO_3$ 20%+HF 4% at room temperature for 60 seconds, followed by rinsing with water;

Electropolishing:
  electrolysis in a polishing solution containing $H_3PO_4$ 45%+$H_2SO_4$ 35%+$H_2CrO_4$ 3% at 50–60° C., under electric current density of 50A/$dm^2$ for about 50 second, and
  dipping in dilute $HNO_3$ for a short period, followed by rinsing with water;

Buff Polishing:
  belt polishing using #180 alumina-silica abrasive grit; and

Bright Annealing:
  heating in an atmosphere of decomposed ammonia gas at about 1,100° C., followed by cooling.

Figure 3:
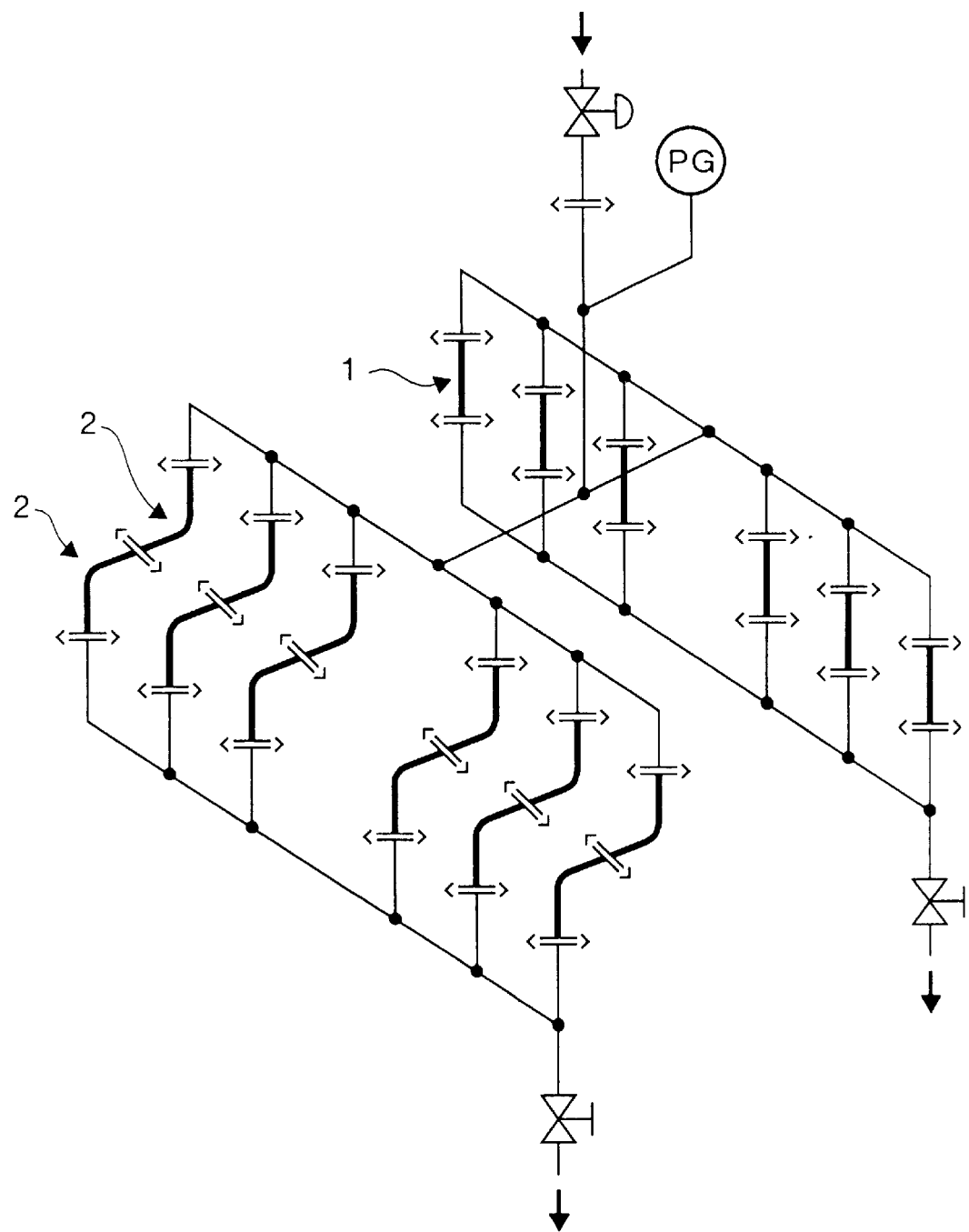
FIG. 3 illustrates scheme of distribution of the sample tubes and elbows as shown in FIGS. 1 and 2 for testing.
Figure 4:
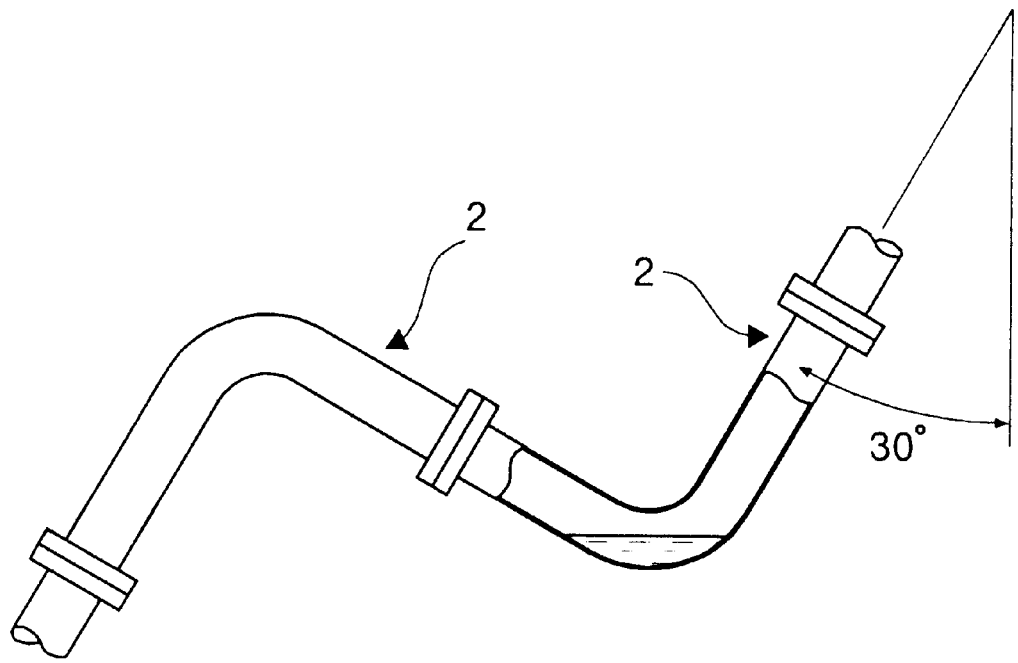
FIG. 4 shows inclination of a part of the samples to be tested in the assembly shown in FIG. 3.

The samples thus surface-treated were assembled as shown in FIG. 3, and pure steam (pressure 2 kg/$cm^2$-gauge) generated by a steam generator was supplied continuously to the assembly. Array of the elbow samples was assembled as shown in FIG. 4 with 30° inclination to the vertical direction so that condensed water may pools in the elbows arranged with downward convex.

Figure 5:
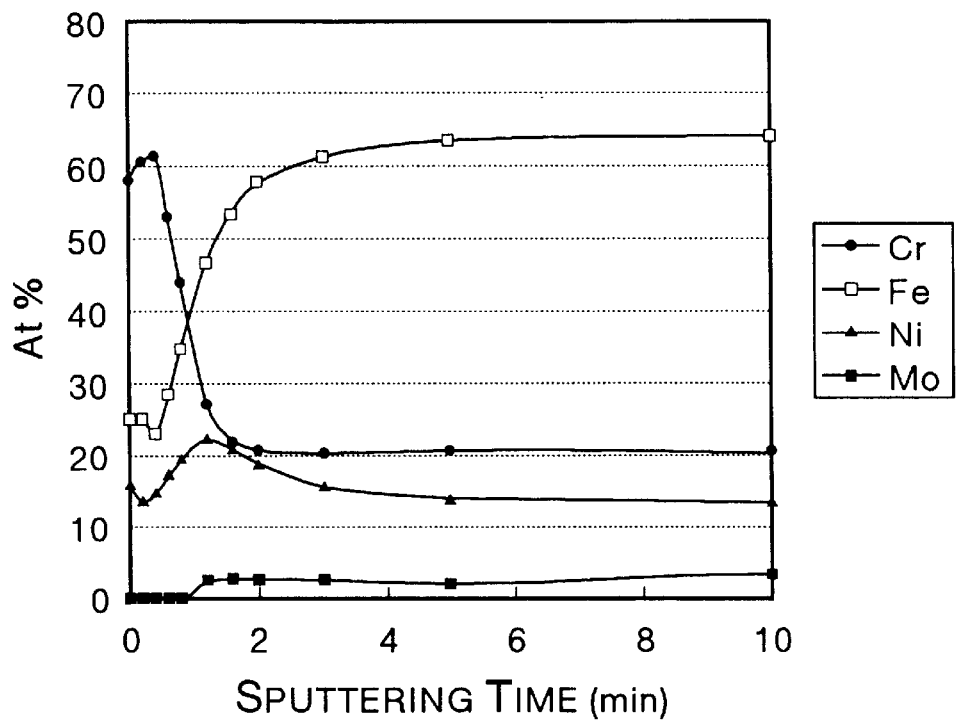
FIG. 5 is a graph showing relation between concentration of each alloying elements in the passivation film formed in the inner surface of the elbow, which was manufactured and tested in the example of the present invention, and the spattering period obtained by AES analysis.
Figure 6:
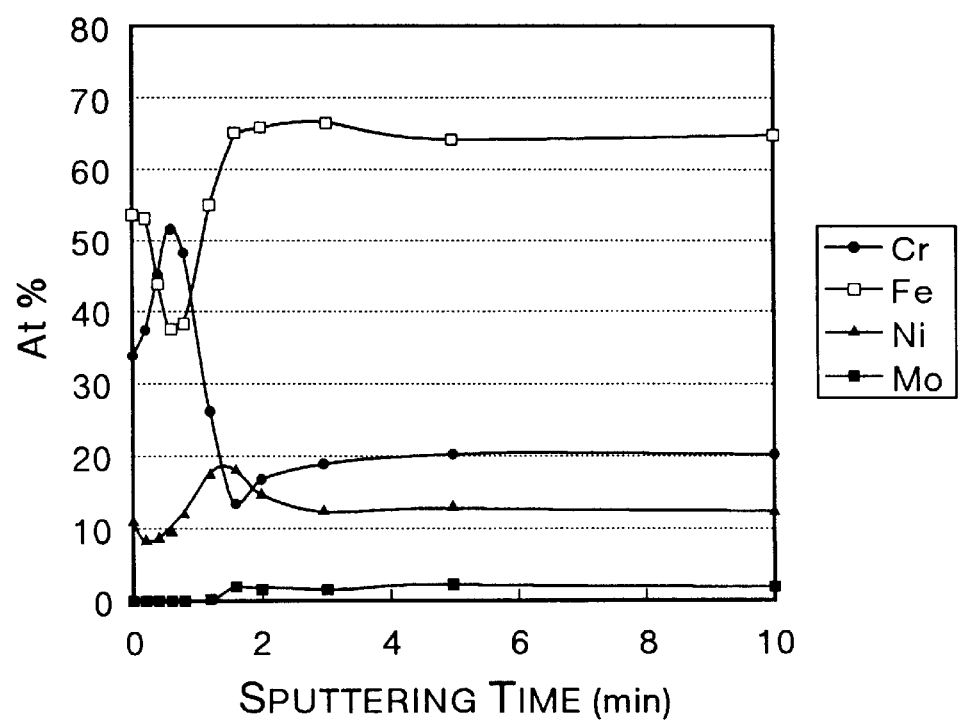
FIG. 6 is a graph showing relation between concentration of each alloying elements in the passivation film formed in the inner surface of the elbow, which was manufactured and tested in the control example of the present invention, and the spattering period obtained by AES analysis.

After 30 days of passing the pure steam the samples were taken from the assemble and cut along the longitudinal direction to observe the inner surfaces of the straight tubes and the elbows. Thickness of the passivation films and Cr-contents thereof were measured, and the Cr/Fe ratios were calculated. For this measurement "Auger" electron spectroscopic analyis (AES) was performed, and the atomic percentages of the main alloying elements of the stainless steel, Fe, Cr, Ni and Mo, were determined from the top layer into the inner part. Changes in the atomic percentages in relation to the spattering time were plotted in graphs, which are shown in FIG. 5 (Run No. 5) and FIG. 6 (Run No. 11).

We regarded the depth at which no further changes in the atomic ratio are observed in these graphs as the boundary, and interpreted that the deeper part beyond the boundary is the matrix alloy and the shallower part to the above boundary is the passivation film consisting of metal oxides. In accordance with this interpretation thickness of the passivation film was determined by relationship between thickness of $SiO_2$ layer which is proportional to the spattering time, and the passivation film thickness. As the Cr-content in the passivation film the maximum value of Cr-content is chosen, and the ratio Cr/Fe was determined as the ratio of the maximum Cr-content and Fe-content at the same depth.

The data obtained by the above AES analysis and the fouling observed are shown in Table 1.

Evaluation in Table 1 corresponds to the extent of fouling as shown in Table. 2.

TABLE 1

| No. | Surface Treatment | Cr-content (at. %) | Atomic Ratio Cr/Fe | Thickness of Passivation Film (A) | Evaluation Straight | Elbow |
|---|---|---|---|---|---|---|
| 1 | Passivation A | 45.5 | 1.48 | 31.4 | Good | Good |
| 2 | Passivation B | 32.4 | 1.32 | 30.8 | Poor | Poor |
| 3 | Passivation C | 58.6 | 1.61 | 38.2 | Excellent | Excellent |
| 4 | Passivation C* | 55.6 | 1.75 | 37.6 | Excellent | Excellent |
| 5 | Passivation D | 40.4 | 1.44 | 38.1 | Acceptable | Acceptable |
| 6 | Passivation E | 35.4 | 1.39 | 39.5 | Poor | Poor |
| 7 | Electrolytic | 40.4 | 1.07 | 21.4 | Poor | Poor |
| 8 | Electrolytic + Passivation A | 46.5 | 1.51 | 33.2 | Good | Good |
| 9 | Electrolytic + Passivation C | 56.6 | 1.77 | 36.7 | Excellent | Excellent |
| 10 | Buff + Passivation C | 53.6 | 1.63 | 37.6 | Poor | Poor |
| 11 | Buff + Electrolytic | 35.5 | 1.34 | 40.2 | Poor | Poor |
| 12 | Buff + Electrolytic + Passivation C | 44.5 | 1.43 | 39.9 | Acceptable | Acceptable |
| 13 | Buff + Bright | 38.4 | 1.03 | 31.2 | Poor | Poor |
| 14 | Buff + Bright + Electrolytic | 43.5 | 1.13 | 21.3 | Poor | Poor |
| 15 | Buff + Electrolytic | 38.5 | 1.35 | 35.3 | Poor | Poor |

Electrolytic = electropolishing
Buff = buff polishing
Bright = bright annealing
*The material used is SUS 304.

TABLE 2

| Evaluation | Straight Tube | Elbow |
|---|---|---|
| Excellent | No discoloration appreciated | No discoloration appreciated. |
| Good | Very small amount of pale red brown speckled stain observed. | Very small amount of pale red brown speckled stain observed |
| Acceptable | Small amount of pale red brown speckled stain observed. | Small amount of pale red brown speckled stain observed, and Black trace at the meniscus observed. |
| Poor | Certain amount of pale red brown speckled stain observed. | Certain amount of pale red brown speckled stain observed, and Black trace at the meniscus observed. |

Based on the above data it is understood that passivation without buff polishing which is a typical mechanical polishing is effective to prevent or reduce the fouling, and that it is necessary to ensure Cr-content of 45 atomic % or higher, preferably, 55 atomic % or higher, in the passivation film. Further it is understood that, even this condition is met, it is advantageous to maintain the atomic ratio of Cr/Fe as high as 1.45 or higher, preferably, 1.70 or higher.

Though the inventors have not yet clarified the mechanism which the mechanical polishing give disadvantage, contrary to the generally accepted idea, it is considered that, in addition to the above discussed surface scratch caused by the abrasive grains and the effect by remaining grains, microstrain caused by the mechanical polishing or accumulation of surface energy give some influence to the surface. As far as the sanitary stainless is concerned, at the time of its appearance, use with highly flattened surface was employed with the intention to prevent adhesion and propagation of microorganisms, and such manner of use has been established. Apparatus related to pure steam is used generally in a closed system and the parts are exposed to a high temperature by which the parts are sterilized. Thus, from the view point of preventing adhesion and propagation of microorganisms there is no particular meaning in making the surface of the stainless smooth. The fact that the mechanical polishing has been nevertheless practiced is interpreted to be a result of a fixed idea by technical tradition and bound by product standards.

It has been known that, after passivation treatment, Cr is concentrated in the passivation film when compared with the original alloy composition. The graph in FIG. 5 is one of the support of this. However, as seen from comparison of FIG. 5 and FIG. 6, even on the stainless steel of the same alloy composition, not only the Cr-content but also the atomic ratio of Cr/Fe are different in the product of passivation without mechanical polishing in accordance with the present invention and in the product of conventional surface treatment. The difference seems to have caused the difference of "excellent" and "poor" in the fouling resistance. Thus, as the conclusion, it is recommended to choose, at manufacturing the pure steam-related apparatus, such treatment that increases Cr-content as well as the atomic ratio of Cr/Fe in the passivation film as high as possible.

Because the pure steam-related apparatus of the present invention is protected from fouling or surface coloring caused by red or black substances, which are considered to be mainly iron oxides, the apparatus may be used as the apparatus for producing material water for injection from the pure steam, possibility of invasion of impurities or solid substance into the product injections is minimized. Also, when used as the high temperature sterilizer, there is no possibility of contaminating the products with the oxides.

In manufacturing of the apparatus it is no longer necessary to carry out the steps of buff polishing and electrolytic polishing which have been traditionally done in the conventional technology. These steps are laborious and elimination of them will largely reduce the investment cost of the apparatus. Even in cases where periodical re-passivation during operation of the apparatus is recommended, necessity of the re-passivation will be considerably lightened. In other words, intervals between the repeated re-passivation can be prolonged. This largely reduces burden of maintenance of the pure steam-related apparatus, and together with the above mentioned reduction of installation cost, enables reduction of total costs of pure steam-related industry.

We claim:

1. An apparatus which treats pure steam comprising a component made of austenitic stainless steel and having a surface which contacts pure steam or a condensate of pure steam, said surface not having been subjected to mechanical surface polishing and being passivated to form a passivation film having a Cr-content of 45 atomic % or higher.

2. The apparatus according to claim 1, wherein the Cr-content in the passivation film is 55 atomic % or higher.

3. The apparatus according to claim 1, wherein the atomic ratio of Cr/Fe in the passivation film is 1.45 or higher.

4. The apparatus according to claim 1, wherein the austenitic stainless steel is selected from the group consisting of SUS 304, 304L, 316, 316L, 316N, 316J1, 316J1L, 317 and 317L.

5. The apparatus of claim 1 selected from the group consisting of a pure steam generator for generating pure steam from purified water, a conduit for pure steam and a sterilizer which uses pure steam.

6. The apparatus according to claim 1, wherein the atomic ratio of Cr/Fe in the passivation film is in the range of 1.61–1.77.

7. A method of manufacturing a component of an apparatus which treats pure steam, said component having a surface which contacts pure steam or a condensate of pure steam, comprising the steps of preparing a blank from an austenitic stainless steel sheet not having been subjected to mechanical surface polishing, forming and welding said blank and passivating a surface of the blank which is to contact the pure steam or a condensate of the pure steam to form a passivation film having a Cr-content of 45 atomic % or higher.

8. The method according to claim 7, wherein the passivation treatment is carried out using an acid solution containing 5 wt. % or more of nitric acid and 1 wt. % or more of hydrofluoric acid.

* * * * *